(12) United States Patent
Wouters et al.

(10) Patent No.: US 11,027,031 B2
(45) Date of Patent: *Jun. 8, 2021

(54) KIT FOR RADIOLABELLING

(71) Applicant: ANMI S.A., Liège (BE)

(72) Inventors: Ludovic Wouters, Herve (BE);
Geoffroy Kaisin, Seraing (BE); André Luxen, Ocquier-Clavier (BE); Marc Léonard, Flémalle (BE); Samuel Voccia, Liège (BE)

(73) Assignee: ANMI S.A., Liège (BE)

( * ) Notice: Subject to any disclaimer, the term of this patent is extended or adjusted under 35 U.S.C. 154(b) by 0 days.

This patent is subject to a terminal disclaimer.

(21) Appl. No.: 16/532,526

(22) Filed: Aug. 6, 2019

(65) Prior Publication Data

US 2019/0361030 A1 Nov. 28, 2019

Related U.S. Application Data

(60) Division of application No. 15/981,951, filed on May 17, 2018, which is a continuation-in-part of application No. 15/505,941, filed as application No. PCT/EP2015/067211 on Jul. 28, 2015.

(30) Foreign Application Priority Data

Aug. 29, 2014 (BE) .................................. 2014/0653

(51) Int. Cl.
| | |
|---|---|
| A61K 51/04 | (2006.01) |
| G01N 33/60 | (2006.01) |
| A61K 51/08 | (2006.01) |
| G21G 1/00 | (2006.01) |

(52) U.S. Cl.
CPC .......... *A61K 51/0482* (2013.01); *A61K 51/08* (2013.01); *A61K 51/088* (2013.01); *G01N 33/60* (2013.01); *G21G 1/0005* (2013.01); *A61K 2123/00* (2013.01)

(58) Field of Classification Search
None
See application file for complete search history.

(56) References Cited

U.S. PATENT DOCUMENTS

| | | | |
|---|---|---|---|
| 4,387,303 | A | 6/1983 | Benjamins |
| 7,011,816 | B2* | 3/2006 | Griffiths ............... A61K 51/088 424/1.11 |
| 7,230,085 | B2* | 6/2007 | Griffiths ............. A61K 47/6849 530/387.3 |
| 8,007,766 | B2 | 8/2011 | Velikyan et al. |
| 2003/0176784 | A1 | 9/2003 | Griffiths et al. |
| 2006/0182687 | A1 | 8/2006 | Yang et al. |
| 2007/0269375 | A1 | 11/2007 | Chen et al. |
| 2012/0009124 | A1 | 1/2012 | Port et al. |
| 2012/0134920 | A1 | 5/2012 | D'Souza et al. |
| 2013/0130537 | A1 | 5/2013 | Keswani |
| 2013/0310537 | A1 | 11/2013 | Mueller |
| 2014/0171637 | A1 | 6/2014 | Fungazza et al. |
| 2018/0230068 | A1 | 8/2018 | Wouters et al. |
| 2018/0230069 | A1 | 8/2018 | Wouters et al. |
| 2018/0267050 | A1 | 9/2018 | Wouters et al. |

FOREIGN PATENT DOCUMENTS

| | | |
|---|---|---|
| JP | 2009-161549 A | 7/2009 |
| RU | 2333557 C2 | 9/2008 |
| WO | 03/059397 A2 | 7/2003 |
| WO | 2008119036 A2 | 10/2008 |
| WO | 2010092114 A1 | 8/2010 |
| WO | 2010141833 A2 | 12/2010 |
| WO | 2013/024013 A2 | 2/2013 |
| WO | 2013024013 A2 | 2/2013 |
| WO | 2014066733 A2 | 5/2014 |
| WO | 2016/030104 A1 | 3/2016 |
| WO | 2016030103 A1 | 3/2016 |
| WO | 2017191604 A2 | 11/2017 |

OTHER PUBLICATIONS

PCT International Search Report and Written Opinion dated Nov. 12, 2015 for PCT International Patent Application No. PCT/EP2015/067211, 12 pages.
Search Report dated Jan. 26, 2015 for Belgian Patent Application No. 2014/0653, 13 pages.
Maus S et al., entitled "Aspects on radiolabeling of 177Lu-DOTA-TATE: After C18 purification re-addition of ascorbic acid is required to maintain radiochemical purity," International Journal of Diagnostic Imaging, 2014, vol. 1, No. 1, pp. 5-12.
Communication Pursuant to Article 94(3) EPC dated Nov. 20, 2018 in connection with European Patent Application No. 15748207.6, 8 pages.
Communication Pursuant to Article 94(3)EPC dated Nov. 20, 2018 in connection with European Patent Application No. 15748208.4, 7 pages.
Haubner, Roland et al: "Development of 68Ga-labelled DTPA galactosyl human serum albumin for liver function imaging", European Journal of Nuclear Medicine and Molecular Imaging, vol. 40, No. 8, Apr. 12, 2013, pp. 1245-1255.
Prinsen, Kristof et al: "Development and evaluation of a 68Ga labeled pamoic acid derivative for in vivo visualization of necrosis using positron emission tomography", Bioorganic & Medicinal Chemistry, vol. 18, No. 14, Jul. 15, 2010, pp. 5274-5281.
Koop, Bernd et al: "Labelling of a monoclonal antibody with 68Ga using three DTPA-based bifunctional ligands and their in vitro evaluation for application in radioimmunotherapy", Radiochimica Acta, vol. 95, No. 1, Jan. 1, 2007, pp. 39-42.

(Continued)

*Primary Examiner* — Jennifer Lamberski
(74) *Attorney, Agent, or Firm* — Amster, Rothstein & Ebenstein LLP (57) ABSTRACT

The present invention relates to a kit for radiolabelling a targeting agent with gallium-68. The present invention also relates to the use of the kit for radiolabelling a targeting agent, and a method for radiolabelling a targeting agent with gallium-68 using the kit.

12 Claims, 4 Drawing Sheets

(56) References Cited

OTHER PUBLICATIONS

Choi, Jae Yeon et al: "Development of Ga-labeled mannosylated human serum albumin (MSA) as a lymph node imaging agent for positron emission tomography", Nuclear Medicine and Biology, vol. 38, No. 3, Sep. 29, 2010, pp. 371-379.
Prata, M. I. M. et al: "Targeting of lanthanide(III) chelates of DOTA-type glycoconjugates to the hepatic asyaloglycoprotein receptor: cell internalization and animal imaging studies", Contrast Media & Molecular Imaging, vol. 1, No. 6, Jan. 1, 2006, pp. 246-258.
Larenkov A. A. et al., "Gallium Radionuclides in Nuclear Medicine: Radiopharmaceuticals Based on 68Ga," Medical radiology and radiation safety, 2011, vol. 56, No. 5, 56-73.
Russian Search Report dated Dec. 19, 2018 in connection with Russian Application No. 2017109582.
Russian Office Action, Dec. 2018, in connection with Russian Application No. 2017109582.
Eppard E et al., entitled "Ethanol-Based Post-processing of Generator-Derived 68Ga Toward Kit-Type Preparation of 68GA-Radiopharmaceuticals," Journal of Nuclear Medicine, vol. 55, No. 6, Jun. 2014, pp. 1023-1028.
Japanese Notification of Reasons for Refusal issued in Application No. 2017-530410, dated Feb. 5, 2019.
Third Party Submission Under 37 CFR § 1.290 for U.S. Appl. No. 15/981,951 dated Mar. 18, 2019.
Office Action dated Nov. 8, 2019 from Russian Patent Application No. 2017109583.
Green et al., "Carbohydrate-Bearing 3-Hydroxy-4-pyridinonato Complexes of Gallium(III) and Indium(III)," Bioconjugate Chem., vol. 16, No. 6, 2005, pp. 1597-1609.
Rizzello et al., "Synthesis and Quality Control of 68GA Citrate for Routine Clinical PET," Nuclear Medicine Communications, vol. 30, No. 7, 2009, pp. 542-545.
Mexican Office Action dated Oct. 27, 2020 from Mexican Patent Appln No. MX/a/2017/002361 (with English language translation attached).
Leyva Ramos et al., "Agentes Quelantes Bifuncionales Utilizados en la Síntesis de Radiofármacos," Rev. Mex. Cienc. Farm., vol. 44, No. 1, Jan.-Mar. 2013, pp. 7-23 (with English language Abstract and concise explanation included in Office Action—see description of reference No. D5).
Australian Examination Report dated Dec. 2, 2019 for Australian Patent Appl. No. 2015309188.
Price E.W. and Orvig C. Matching chelators to radiometals for radiopharmaceuticals. Chemical Society Reviews, vol. 43, No. 1, Jan. 7, 2014, pp. 260-290.
International Search Report and Written Opinion dated Nov. 13, 2015 in PCT International Appln. No. PCT/EP2015/067213.
Russian Office Action dated Nov. 8, 2019 in Russian Application No. 2017109582 with English language translation.
Cerchiaro et al., "Investigations of Different Carbohydrate Anomers in Copper(II) Complexes With D-Glucose, D-Fructose, and D-Galactose by Raman and EPR Spectroscopy," Carbohydrate Research, vol. 340, Aug. 25, 2005, pp. 2352-2359.
Norkus, "Metal Ion Complexes With Native Cyclodextrins. An Overview," J. Incl. Phenom. Macrocycl. Chem., vol. 65, Apr. 30, 2009, pp. 237-248.

* cited by examiner

KIT FOR RADIOLABELLING

CROSS-REFERENCE TO RELATED APPLICATIONS

This application is a divisional of U.S. application Ser. No. 15/981,951, filed May 17, 2018, which is a continuation-in-part of U.S. application Ser. No. 15/505,941, filed Feb. 23, 2017, which is a U.S. national phase of PCT Application No. PCT/EP2015/067211, filed Jul. 28, 2015, which claims priority to Belgian Patent Application No. 2014/0653, filed Aug. 29, 2014, the contents of which are hereby incorporated by reference.

TECHNICAL FIELD

The present invention is related to kit for radiolabelling.

BACKGROUND

Recently, some very interesting clinical results based on gallium-68 radiolabeled molecules for imaging in vivo by PET were published and presented. These radiotracers are generally made by assembly of a chelating agent with a targeting agent, generally DOTA-functionalized targeting agents, allowing, respectively, the reaction with a metallic radioisotope or radiometal and biological/metabolic activity of the radiotracer. However, due to the short half-life of gallium-68 (68 minutes), the radiotracer, i.e. radiolabelled chelate-functionalized targeting agent, based on this radioisotope are not suitable for long-distance distribution and require on the spot production and suitable production equipment, such as automated synthesizers, for the radiolabelling process, making it difficult for widespread use in routine nuclear medicine.

The labelling reaction with the gallium-68 is performed by chelating the radioactive metal with a suitable chelating agent in a suitable reaction medium, usually in a buffered medium in order to ensure an optimum pH for both the chelation reaction and the gallium solubility.

Gallium-68 itself is obtained from a generator. Said generator is an alternative to the in situ production using a cyclotron or daily delivery of radioisotopes. The system was initially developed for technecium-99. The principle is based on the radiochemical separation between a parent element of long half-life (or nonradioactive elements such as germanium-68) contained in the generator and a daughter element which is a short half-life element resulting from the disintegration of the parent element. The daughter is recovered with excellent radiochemical purity and radionuclidic properties (i.e. without contamination from other radionuclides or other radiochemical impurities) and with good chemical purity (low metal ion content). This separation is made possible by the different chemical properties of the two elements (parent and daughter).

The characteristics of a germanium-68/gallium-68 generator can be summarized as follows:
  The eluate is obtained in an acid solution (0.05M-5M HCl, or specified by the manufacturer of the generator)
  The eluate contains zinc-68, resulting from both the manufacturing process of germanium-68 and disintegration of gallium-68, whose concentration increases continuously in function of time elapsed since the last elution of the generator. Indeed, this zinc-68 accumulates in the generator. This can be detrimental to the performance of radiolabelling since this zinc-68 enters in direct competition with gallium-68 for chelation reactions used for radiolabelling.
  The eluate further contains germanium-68 (the "breakthrough") released from the generator.
  The eluate also contains a variety of metal leaching from the solid phase of the generator column, tubings, but also brought by the HCl used for elution:
    Microg/ml level: Fe (III), Zn (II), Al (III)
    Picog/L level: Mn (II), Pb (II), Ti (IV), Cr (III), Ni (II) (Sn (IV))

The efficiency of the chelation reaction is dependent on a suitable pH, but also on possible competition of the metallic impurities mentioned above with the gallium-68 during the chelation reaction as well. In addition, it is generally accepted that heat facilitates the chelation reaction for the most commonly used gallium-68 based radiotracers.

In the state of the art, the presence of metal ions that compete with gallium-68 is generally reduced by pre-labelling purification or fractionation of the eluate (as described in WO 2010/092114). These additional steps however represent a loss of radioactivity resulting from, either wasted time or the process itself. These losses can reach up to 30% of the total radioactivity, respectively, 10% due to decay and 20% coming from the pre-purification process itself.

The possibility of partial chelation of gallium-68 requires, in general, a final post-labelling purification in order to obtain a radiotracer having a radiochemical purity that meets the pharmaceutical specifications (>90% radiochemical purity). These steps also represent an additional loss of activity that can rise to up to 10% resulting from wasted time or the process itself.

According to known processes, at the end of the radiolabelling, a sequestering agent having a particular affinity for the gallium-68 may be added to chelate the non-reacted part of the isotope. This complex formed by the sequestering agent and the non-reacted gallium-68 is then discarded in order to reach a better radiochemical purity after radiolabelling.

In addition, the need for these pre- and post-labelling purification steps makes these gallium-68 labeled radiotracer synthesis dependent, to some extent, on automation and on the use of a synthesis module. In addition to technical expertise, this requires extra time loss unfavorable to the overall performance.

Due to the short half-life of the Gallium-68 radionuclide (68 minutes) and to the limited activity supplied by the generator (max. 100mCi), any improvement in order to achieve rapid, direct and high efficiency chelation of target molecules is thus highly desirable.

In order to maintain the pH of the labelling solution in a range where it is possible to ensure both the chelating reaction and the gallium-68 solubility, a buffering medium is generally used. The desired buffer must be nontoxic, must effectively maintain the pH within a range of 3.0 to 5.0, should not compete with gallium-68 ions and have preferably a low capacity for metal chelation with regard to the capacity of the chelating agent as assembled with the targeting agent. It must also be able to tolerate possible small changes in the volume of generator eluate (and therefore the amount of HCl), i.e. it must be strong enough to maintain the pH within the desired range with 10% changes in the volume of eluate.

Management of competing metal impurities is another challenge. It has been shown in WO2013024013 that adding a co-chelating agent could allow inhibition of competing metal impurities. Indeed, any species that would inhibit metal impurities by avoiding or having limited capacity to interfere negatively on the gallium-68 chelation reaction can act as a trap for these impurities. In other words, this inhibitory effect brings the apparent concentration of competitor metal, i.e. the concentration of metallic impurities yet available for chelation to a level which allows high yields and reproducible radiolabelling. This co-chelating agent is by definition different than the chelating agent assembled with the targeting agent.

In this context, it is clear that a need exists for an improved process for the preparation of $^{68}$Ga complex which overcomes one or more of the above mentioned problems. This involves identifying an appropriate medium that maintains the pH within a tolerable range, to handle the metal contamination, which avoids the need to heat for promoting the chelating reaction and allows gallium-68 chelation yields upper 90%. In addition, the sequence of the steps performed and the assembly of the kit for performing all steps without being exposed to radioation during the labelling process is very important.

SUMMARY OF THE INVENTION

The present inventors have developed a user-friendly, time-saving radiolabelling kit which reduces the risk of exposure of the user to the buffering medium, the targeting agent and/or the radioactive material; which allows to radiolabel target agents at a temperature near or equal to room temperature; and/or which allows to directly elute gallium-68 in the kit and performing the radiolabelling reaction without the need for any prior or subsequent operation.

More particularly, the present inventors found that the use of the kit in an assembly with a self-shielded device, especially a self-shielded device comprising an invertible container unit comprising a void space for holding a vial and a channel configured to hold a dismountable conduit for connecting the vial within the self-shielding device to an environment external of the self-shielded device, allows to radiolabel a targeting agent and to withdraw a dose of the radioactive-labelled targeting agent or to guide a dose of a radioactive-labelled targeting agent to a patient by using the force of gravity, thereby avoiding the need to pressurize a vial comprising the radioactive-labelled targeting agent (for example by use of a pump) and reducing risk of exposure of the user to radioactive material. The present invention relates to the following aspects:

Aspect 1. A radiolabelling kit comprising:
a first vial, wherein said vial is empty and vacuum;
a second vial, wherein said second vial comprises a suitable amount of acetate buffer for balancing the pH of the eluate from a gallium-68 generator to a pH value ranging from 3 to 5 when said generator is eluted in the kit; and
a third vial, wherein said third vial comprises a lyophilized chelate-functionalized targeting agent and a lyophilized metal inhibitor.

Aspect 2. The radiolabelling kit according to aspect 1, wherein the chelate-functionalized targeting agent is prostate-specific membrane antigen (PSMA)-targetting peptide.

Aspect 3. The radiolabelling kit according to aspect 1 or 2, wherein the metal inhibitor is selected from the group comprising: DOTA and its derivatives, DTPA and its derivatives, and sugars.

Aspect 4. The radiolabelling kit according to any one of aspects 1 to 3, wherein the metal inhibitor is sugar selected from the group comprising: monosaccharides and their derivatives, disaccharides and their derivatives, and polysaccharides and their derivatives and sulfated sugars.

Aspect 5. The radiolabelling kit according to any one of aspects 1 to 4, wherein the kit comprises one or more of the list consisting of:
a needleless transfer device for connecting two vials;
an extension line comprising a proximal end adapted for connecting the extension line to the vial adapter and a distal end adapted for connecting the extension line to the needleless syringe;
a vial adapter adapted for connecting the extension line or a needleless syringe to a vial; and
a needleless syringe.

Aspect 6. An assembly comprising the kit according to anyone of aspects 1 to 5 and a self-shielded device configured to hold said first vial.

Aspect 7. The assembly according to aspect 6, further comprising a gallium-68 generator.

Aspect 8. The assembly according to aspect 6 or 7, wherein the self-shielded device is invertible.

Figure 1A:
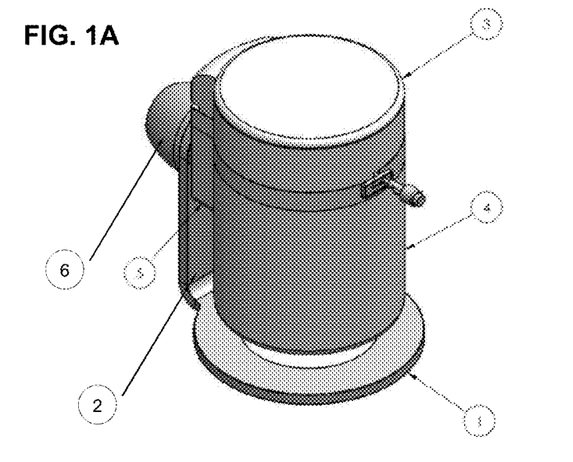
FIG. 1A-1C illustrates an exemplary shielding device comprising a support (2) comprising a base (1), a lid (3), a vessel (4), and a pivot point (5) attached to the support, suitable for the assembly and method for radiolabelling a targeting agent with gallium-68 as described herein. (A) top-front view, (B) top-back view, (C) lateral view.
Figure 1B:
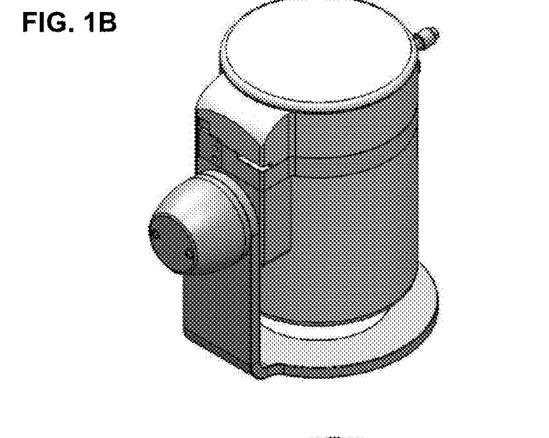
Figure 1C:
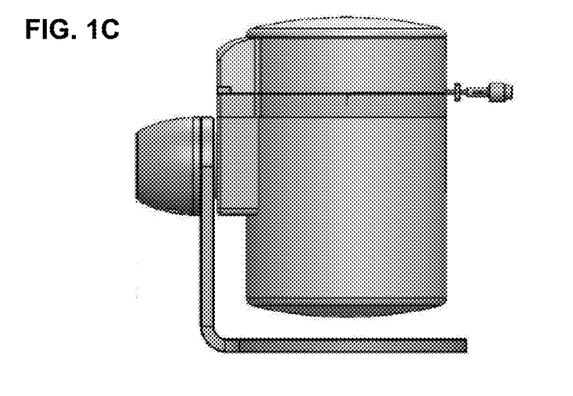

Aspect 9. The assembly according to any one of aspects 6 to 8, wherein the self-shielded device comprises a support (2) and a container unit (4), wherein said container unit comprises a lid (3) and a vessel comprising a void space dimensioned to hold said first vial; and wherein the support comprises a base (1) and extending from the base and in fixed relation to the base at least one longitudinal member (6).

Aspect 10. The assembly according to aspect 9, wherein the dimensions of the void space suitable for holding the vial are at most 10% larger than the dimensions of the vial.

Aspect 11. The assembly according to aspect 9 or 10, wherein the at least one longitudinal member (6) is provided in revolute attachment with respect to the vessel, where an axis of rotation is horizontal, non-parallel to a central axis of the vial and/or parallel to an underside of the base (1).

Aspect 12. The assembly according to any one of aspects 9 to 11, wherein the lid (3) is in revolute attachment with respect to the vessel, where an axis of rotation is vertical, parallel to a central axis of the vial and/or non-parallel to an underside of the base (1).

Aspect 13. The assembly according to any one of aspects 9 to 12, wherein the container unit (4) is provided with a channel configured to hold a dismountable conduit for connecting the vial within the self-shielding device to an environment external of the self-shielded device, preferably wherein the channel configured to hold a dismountable conduit is provided at the interface of the lid (3) and the vessel.

Aspect 14. Use of the kit according to any one of aspects 1 to 5 or the assembly according to any one of aspects 6 to 13, for radiolabelling a chelatefunctionalized targeting agent with gallium-68 carried out at a temperature near or equal to room temperature.

Aspect 15. A method for radiolabelling a chelate-functionalized targeting agent with gallium-68, comprising the elution of a gallium-68 generator with an eluent comprising HCL, in a kit according to any one of aspects 1 to 5 or an assembly according to any one of aspects 6 to 13.

Aspect 16. A method for radiolabelling a chelate-functionalized targeting agent with gallium-68, comprising
recovering an eluate of a gallium-68 generator into a first vial located within a self-shielded device, preferably wherein said first vial is a vacuumed vial;
adding a suitable amount of acetate buffer to the lyophilized chelate-functionalized targeting agent and lyophilized metal inhibitor comprised in a second vial to balance the pH of the eluate from a gallium-68 generator to a pH value ranging from 3 to 5 when said mixture of acetate buffer, chelate-functionalized targeting agent and metal inhibitor is contacted with the eluate;

recovering the mixture of acetate buffer, chelate-functionalized targeting agent and metal inhibitor from the second vial;

adding the mixture of acetate buffer, chelate-functionalized targeting agent and metal inhibitor to the recovered eluate of the gallium-68 generator comprised in the first vial located within the shielding device; and allowing radiolabelling of the chelate-functionalized targeting agent with gallium-68.

Aspect 17. The method according to aspect 16, wherein the step of allowing radiolabelling of the chelate-functionalized targeting agent with gallium-68 is performed for at least 1 minute, preferably for at least 5 minutes.

Aspect 18. The method according to aspect 16 or 17, wherein the first vial located within the self-shielded device is connected to a vial adapter which is connected to an extension line comprising a proximal end adapted for connecting the extension line to the vial adapter and a distal end adapted for connecting the extension line to a needleless syringe; wherein said distal end is located outside the self-shielded device.

Aspect 19. The method according to any one of aspects 16 to 18, wherein the suitable amount of acetate buffer is contained in a third container and the suitable amount of acetate buffer is added to the lyophilized chelate-functionalized targeting agent and lyophilized metal inhibitor by interconnecting said second and third vial via a needleless transfer device.

Aspect 20. The method according to aspect 19, wherein the needleless transfer device comprises a valve and a luer-lock.

Aspect 21. The method according to aspect 20, wherein the step of adding a suitable amount of acetate buffer present in a third vial to the lyophilized chelate-functionalized targeting agent and lyophilized metal inhibitor comprised in a second vial comprises:

interconnecting the third vial comprising the acetate buffer and the second vial comprising lyophilized chelate-functionalized targeting agent and lyophilized metal inhibitor by a needleless transfer device; wherein the third vial is located above the second vial, wherein the luer-lock is capped, and wherein the valve can be configured to be in fluid communication with the third vial and the luer-lock, the second vial and the luer-lock, or the third and second vials and the luer-lock;

allowing the acetate buffer to flow from the third vial to the second vial through the valve of the needleless transfer device which is configured to be in fluid communication with the third and second vials and the luer-lock; and mixing the acetate buffer, lyophilized chelate-functionalized targeting agent and lyophilized metal inhibitor.

Aspect 22. The method according to aspect 20 or 21, wherein the step of recovering the mixture of acetate buffer, chelate-functionalized targeting agent and metal inhibitor from the second vial comprises:

configuring the valve of the needleless transfer device to be in fluid communication with the second vial and the luer-lock, but not in fluid communication with the third vial, wherein the luer-lock is capped;

uncapping the luer-lock;

connecting a needleless syringe comprising air in a volume which is at least 50% the volume of the second vial to the uncapped luer-lock;

injecting the air in a volume which is at least 50% the volume of the second vial from the needleless syringe into the second vial via the uncapped luer-lock;

turning the third vial and the second vial interconnected by the needleless transfer device so that the second vial is located above the third vial; and withdrawing the mixture of acetate buffer, chelate-functionalized targeting agent and metal inhibitor from the second vial via the uncapped luer-lock, using the needleless syringe.

Aspect 23. The method according to any one of aspects 16 to 22, wherein the step of adding the mixture of acetate buffer, chelate-functionalized targeting agent and metal inhibitor to the recovered eluate of the gallium-68 generator comprised in the first vial located within the self-shielded device comprises injecting the mixture of acetate buffer, chelate-functionalized targeting agent and metal inhibitor into the first vial located within the self-shielded device using a needleless syringe.

Aspect 24. The method according to any one of aspects 16 to 23, wherein the self-shielded device comprises a container unit comprising a void space dimensioned to hold the first vial, wherein said container unit is rotatable around a horizontal axis.

Aspect 25. The method according to aspect 24, further comprising inverting the container unit; and withdrawing the gallium-68-labelled chelate-functionalized targeting agent from the first vial.

FIGURES OF THE INVENTION

DETAILED DESCRIPTION

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. The terms also encompass "consisting of" and "consisting essentially of".

The recitation of numerical ranges by endpoints includes all numbers and fractions subsumed within the respective ranges, as well as the recited endpoints.

The term "about" as used herein when referring to a measurable value such as a parameter, an amount, a temporal duration, and the like, is meant to encompass variations of and from the specified value, in particular variations of +/−10% or less, preferably +/−5% or less, more preferably +/−1% or less, and still more preferably +1-0.1% or less of and from the specified value, insofar such variations are appropriate to perform in the disclosed invention. It is to be understood that the value to which the modifier "about" refers is itself also specifically, and preferably, disclosed.

Whereas the term "one or more", such as one or more members of a group of members, is clear per se, by means of further exemplification, the term encompasses inter alia a reference to any one of said members, or to any two or more of said members, such as, e.g., any ≥3, ≥4, ≥5, ≥6 or ≥7 etc. of said members, and up to all said members.

All documents cited in the present specification are hereby incorporated by reference in their entirety.

Unless otherwise specified, all terms used in disclosing the invention, including technical and scientific terms, have the meaning as commonly understood by one of ordinary skill in the art to which this invention belongs. By means of further guidance, term definitions may be included to better appreciate the teaching of the present invention.

In the following passages, different aspects or embodiments of the invention are defined in more detail. Every aspect or embodiment so defined may be combined with each of the other aspects or embodiments unless stated otherwise. In particular, any feature indicated as being preferred or advantageous in one embodiment may be combined with any other embodiment or embodiments indicated as being preferred or advantageous.

The present invention overcomes one or more of the problems identified and observed in the state of the art and allows the direct radiolabelling of a chelate-functionalized targeting agent with gallium-68 at a temperature below 50° C. and preferably at room temperature, using a kit as described herein, this gallium-68 being eluted from a germanium-68/gallium-68 generator in an acidic aqueous solution.

Accordingly, in one aspect, the invention provides a kit comprising:
  A suitable amount of acetate salt to balance at least the acidic pH eluate from a gallium-68 generator to a pH value ranging from 3 to 5 when said generator is eluted in the kit; and
  A chelate-functionalized targeting agent, able to chelate gallium-68 in the radiolabeling conditions
  A metal inhibitor, which is a co-chelating agent, capable of inactivating metals other than gallium-68 without interfering with the chelation between gallium-68 and the said chelate-functionalized targeting agent, under the conditions of the labelling reaction. In other words, said metal inhibitor is selected for its ability to chelate contaminating metals interfering and competing with the chelation of gallium-68 while being mostly unable gallium-68 in the said conditions of the labelling reaction as opposed to the chelate-functionalized targeting agent.

Said kit being suitable to perform the radiolabelling reaction of said chelate-functionalized targeting agent with gallium-68 as carried out at a temperature near or equal to room temperature, preferably at a temperature below 50° C. and more preferably at room temperature.

The invention also relates to a kit wherein the acetate salt, the chelate-functionalized targeting agent and the metal inhibitor are (co-) lyophilized.

The invention also relates to a kit wherein the chelate-functionalized targeting agent and the metal inhibitor are (co-)lyophilized, the acetate salt being added subsequently.

The invention also relates to a kit wherein the chelate-functionalized targeting agent and the metal inhibitor are (co-)lyophilized, an acetate buffer being added subsequently.

The invention also relates to a kit wherein the acetate salt, the chelate-functionalized targeting agent and the metal inhibitor are solubilized and further frozen.

The kit as described herein can not only provide an optimum pH for carrying out the chelation reaction or radiolabelling, but also allows to tolerate or manage the variation of the eluate volume and acidity associated with different types of gallium-68 generators, through the use of a suitable amount of acetate salt that when mixed with the acid generator eluate, form an acetic acid/acetate buffer having an acid pH comprised in the interval 3-5. In these conditions, the amount of non-chelated gallium-68 because of a too low or too high pH, which leads respectively to a high content of free gallium-68 cations or to gallium-68 hydroxides (gallium colloids), is minimized.

In addition, the acetate buffer is well tolerated as a buffer or as an excipient for pharmaceuticals.

Furthermore, the present inventors have found that a metal inhibitor can be used in the radiolabelling method for neutralizing, at least partially, interfering species and allows the gallium-68 to react with the chelate-functionalized targeting agent. These metal inhibitors may temporarily or permanently remove metals that compete with gallium-68 for the reaction with the chelate-functionalized targeting agent. Said metal inhibitor is thus unable to chelate gallium-68 in the said conditions of the labelling reaction, but chelate other metals interfering with the chelation of gallium-68 by the chelate-functionalized targeting agent. The presence of a metal inhibitor during the radiolabelling reaction provides an advantageous alternative to current approaches for managing the presence of metallic impurities, such as increasing the amount chelate-functionalized targeting agent, or the pre-treatment of the eluate of the generator, since these additional purification steps consume time (and radioactivity).

These aspects as described herein advantageously allow obtaining an appropriate chelation yield, particularly of about 90% and more, and therefore a sufficient radiochemical purity without any preliminary or further final purification.

The presence of a chelate-functionalized targeting agent, an acetate salt and a metal inhibitor in the kit advantageously allows to directly elute gallium-68 generator in the kit and performing the radiolabelling reaction without the need for any prior or subsequent operation.

In addition, all kit components as described herein can be lyophilized altogether or frozen which ensures a longer shelf life.

Thus, the main advantages of a kit as disclosed herein that differentiate said kit from the state of the art are:
  A completely dry or frozen kit that allows a better shelf life of the chelate-functionalized targeting agent;
  The possibility of radiolabelling without the need for an automated synthesizer;
  The possibility of a radiolabelling without the need for heating;
  The presence of a metal inhibitor which advantageously allows to use less chelate-functionalized targeting agent and allowing the implementation of more affordable radiopharmaceutical synthesis;
  The presence of a metal inhibitor which advantageously allows to improve the radiolabelling yields;
  The fact that any brand generator can be used with this kit provided as acetate or partially neutralized with HCl so that when mixed with the acid generator eluate, the optimal pH for the radiolabelling is obtained.

As used herein, "acetate" refers to the anionic molecule $CH_3COO-$. The term "acetate salt" herein is meant any metal salt acetate. Non-limiting examples of acetate salts include sodium acetate, potassium acetate, aluminium acetate, and ammonium acetate. Preferably sodium acetate is used in the kits as described herein. Said acetate salt can be present in solid form or can be comprised in a buffered solution or buffer.

The amount of salt of the acetate present in the kit as described herein can be adapted according to the type and/or the kind of gallium-68 generator, in particular the quantity of acetate salt present in the kit is able to balance the pH, i.e. to manage the quantity of HCl as eluted from a gallium-68 generator such that the resulting solution has a pH between 3 and 5, preferably between 3.5 and 4.7, preferably between 3.9 and 4.5.

Alternatively, the kit as described in the present invention may comprise a fixed quantity of acetate salt. The amount of HCl differences from the generator eluate (depending on the type and/or the generator brand gallium-68) can then be adjusted by adding an appropriate amount of HCl to the kit as described herein prior to elution. The amount of HCl added to the kit as described in the present invention is partially neutralizing the acetate salt such that the non-neutralized acetate salt is able to balance the pH of a quantity of HCl from a generator eluate such that the resulting solution has a pH between 3 and 5, preferably between 3.5 and 4.7, preferably between 3.9 and 4.5.

Preferably, the acetate salt is present in the kit as taught herein in an amount between about 1 mg and about 1000 mg, preferably in an amount between about 10 mg and about 750 mg, more preferably in an amount between about 20 mg and about 500 mg.

Metal inhibitors used in the present invention are selected for their ability to inhibit the competing metals, without (substantially) inhibiting gallium-68 ions in their chelation reaction with the chelate-functionalized targeting agent. Indeed, these metal inhibitors should (substantially) not interfere negatively on the main radiolabelling reaction or lead to the formation of secondary radiolabeled species. In other words metal inhibitors should have a limited or no capacity to complex gallium-68 in the conditions used for the radiolabelling reaction, i.e. below 50° C. in an acetate buffer between pH 3 and pH 5. Limited means at least 100 times less than the chelating agent used for the chelate-functionalized targeting agent.

It is interesting to note that the function of metal inhibitors in the present invention is the opposite of the function of the sequestering agents used in the prior art. Indeed, according to known methods, at the end of the labelling reaction, a sequestering agent having a particular affinity for the gallium-68 may be added to chelate the unreacted portion of the isotope, whereas, according to the present invention an agent capable of reducing the competition of metallic impurities other than the gallium-68 is added at the beginning of the reaction.

In addition, being able to perform the radiolabelling reaction at a temperature close to room temperature (<50° C.) advantageously allows the use of metal inhibitors that would not be usable at the usual temperatures of radiolabelling DOTA-functionalized targeting agents by such as used in WO2013024013, because they would be entering in direct competition with gallium-68 at such temperatures of above 50° C. The temperature is therefore also described in the invention as a parameter for adjusting the reactivity of the metal inhibitor.

As used herein, a "metal inhibitor" refers to any molecule capable of interacting with, or competing metals, or the chelating moiety of the chelate-functionalized targeting agent or with gallium-68 directly, to inhibit wholly or partially the chelation the chelate-functionalized targeting agent said competing metals and/or promote the chelating of gallium-68 by said targeting agent. Such metal inhibitors should have a limited or no capacity to complex gallium-68 in the conditions used for the radiolabelling reaction, i.e. below 50° C. in an acetate buffer between pH 3 and pH 5. Limited means at least 100 times less than the chelating agent used for the chelate-functionalized targeting agent.

Metal inhibitors are preferably selected from the group comprising or consisting of: DOTA and its derivatives, such as, DOTATOC, DOTANOC, DOTATA, TRITA, DO3A-Nprop, BisDO3A and TrisDO3A; DTPA and its derivatives such as tetra-tBu-DTPA, p-SCN-Bz-DTPA, MX-DTPA and CHX-DTPA; and sugars. Sugars used as metal inhibitors in the kit of the invention can be monosaccharides or derivatives of monosaccharides such as tetracetose, pentacetose, hexacétose, tetrose, pentose, hexose, D-mannose, D-fructose, and derivatives; and/or disaccharides and their derivatives such as maltose and its derivatives; and/or polysaccharides and their derivatives such as dextrins, cyclodextrins, cellulose and derivatives thereof.

Preferably, the metal inhibitor is present in the kit as described herein in micromolar amounts, preferably in nanomolar quantities, preferably in an amount of less than 500 nanomolar, still more preferably in an amount less than 100 nanomoles.

It is important to note that metal inhibitors as shown above can also be advantageously used in chelation reactions wherein other buffers than buffered acetic acid/acetate are used.

Metal inhibitors as shown above can also be advantageously used in chelation reactions wherein said metal inhibitor is included in the eluent generator, in the HCl solution, or in water possibly added before elution of the generator. Said metal inhibitor is thus found in the radiolabelling solution. The metal inhibitor may also be chemically bound to the chelate-functionalized targeting agent. This chemical bond can or cannot be a labile bond under the conditions of radiolabelling with the chelate-functionalized targeting agent. This means that in the conditions of radiolabelling the metal inhibitor is formed and released in situ. Examples of such preferred bonds are . . .

As used herein, a "chelate-functionalized targeting agent" refers to a targeting agent capable of being labeled with a radioisotope such as for example gallium-68, by means of a chelating agent which is bound to the targeting molecule.

Preferred chelating agents for functionalizing a targeting agent to be radiolabeled with gallium-68 are those which form stable chelates with Ga3+, in particular 68-Ga3+(the radioisotope generator eluted from a germanium-68/gallium-68 generator using HCl), at least for a time sufficient for diagnostic investigations using such radiolabelled targeting agents.

Suitable chelating agents include aliphatic amines, linear or macrocyclic such as macrocyclic amines with tertiary amines. While these examples of suitable chelating agents are not limited, they preferably include the NOTA and its derivatives, such as TACN, TACN-TM, DTAC, H3NOKA, NODASA, NODAGA, NOTP, NOTPME, PrP9, TRAP, Trappist Pr, NOPO, TETA; Tris(hydroxypyridinone) (THP) and derivatives, chelates open chain such as HBED, DFO or desferrioxamine or desferal, EDTA, 6SS, B6SS, PLED, TAME, YM103; NTP (PRHP) 3; the H2dedpa and its derivatives such as H2dedpa-1, 2-H2dedpa, H2dp-bb-NCS, and H2dp-N-NCS; (4,6-MeO2sal) 2-BAPEN; and citrate and derivatives thereof.

The chelate-functionalized targeting agent can be a peptide, for example, a peptide comprising 2 to 20 amino acids, a polypeptide, a protein, a vitamin, a saccharide, for example a monosaccharide or a polysaccharide, an antibody and its derivatives such as nanobodies, diabodies, antibodies fragments, nucleic acid, an aptamer, an antisense oligonucleotide, an organic molecule, or any other biomolecule that is able to bind to a certain diagnostic target or to express a certain metabolic activity.

Chelate-functionalized targeting agents as described herein preferably have a capacity of biological targeting. Non-limiting examples of suitable targeting agents include molecules that target VEGF receptors, analogs of bombesin or gastric-releasing peptide (GRP) receptor targeting molecules, molecules targeting somatostatin receptors, RGD peptides or molecules targeting $\alpha v \delta 3$ and $\alpha v \delta 5$, annexin V or molecules targeting the apoptotic process, molecules targeting estrogen receptors, biomolecules targeting the plaque, prostate-specific membrane antigen (PSMA)-targeting peptides, Bombesin (BN), aminopeptidase N-targeting peptides, peptide transporter 1-targeting peptides, epidermal growth factor (EGF) receptor-targeting peptides, Mucin1-targeting peptides (e.g. GO-201), urokinase plasminogen activator receptor-targeting peptides (e.g AE105), cholecystokinin receptor-targeting peptides (e.g. CCK8), neurotensin receptor-targeting peptides (e.g. neurotensin), transferrin receptor-targeting peptides, vascular endothelial growth factor receptor-targeting peptides (e.g. peptide K237, SP 5.2, . . . ), retinoblastoma-targeting peptides, or ephrin receptor-targeting peptides. More generally, a list targeting molecules, organic or not, functionalized by a chelating agent can be found in the journal of Velikyan et al., Theranostic 2014, Vol. 4, Issue 1 "Prospective of 68Ga-Radiopharmaceutical Development", hereby incorporated by reference.

In some embodiments, the metal inhibitor is included in the eluent generator, in the HCl solution, or possibly in the added water prior to elution of the generator. Said metal inhibitor and is thus found in the radiolabelling solution.

The various components of the kit as described herein are preferably present in a container or vial, preferably a siliconized glass vial. However, also a kit wherein the individual components are present in separate containers or vials is envisaged.

The invention further provides a radiolabelling kit comprising:
- a first vial, wherein said vial is empty and contains a vacuum;
- a second vial, wherein said second vial comprises a suitable amount of acetate buffer for balancing an eluate from a gallium-68 generator to a pH value ranging from 3 to 5 when said generator is eluted in the kit; and
- a third vial, wherein said third vial comprises a lyophilized chelate-functionalized targeting agent and a lyophilized metal inhibitor.

When the radiolabeling kit is used in a method for radiolabeling of a chelate-functionalized targeting agent as described herein with an eluate of a gallium-68 generator, the presence of a vacuum in the first vial will reduce the risk of exposure of the user to the radioactive material.

In particular embodiments, the first, the second and the third vials are siliconized glass vials.

In particular embodiments, the first, the second and the third vials are sealed by a pierceable rubber stopper.

In particular embodiments, the first, the second and the third vials have a height of at least 4 cm, at least 5 cm, at least 6 cm, at least 7 cm, at least 8 cm, at least 9 cm or at least 10 cm. For example, the first, the second and the third vials may have a height of about 5 cm, 5.5 cm, 6 cm, 6.5 cm, 7 cm, 7.5 cm, or 8 cm.

In particular embodiments, the first, the second and the third vials are vials with a diameter of at least 10 mm, at least 15 mm, at least 20 mm, such as a diameter of 15 mm, 16 mm, 17 mm, 18 mm, 19 mm, 20 mm, 21 mm, 22 mm, 23 mm, 24 mm or 25 mm. Preferably, the first, the second and the third vials are vials with a diameter of 20 mm.

In particular embodiments, the first, the second and the third vials are vials with a volume of at least 5 ml, at least 10 ml or at least 20 ml, such as a volume of 5 ml, 6 ml, 7 ml, 8 ml, 9 ml or 10 ml.

In particular embodiments, the acetate buffer is lyophilized and is present in an amount of between 100 and 200 mg, such as abot 150 mg.

In particular embodiments, the second vial of the kit further comprises a stabilizer which is able to protect the chelate-functionalized targeting agent from radiolysis upon radiolabelling said chelate-functionalized targeting agent with gallium-68. Non-limiting examples of suitable stabilizers are ethanol, gentisic acid and ascorbic acid.

In particular embodiments, the chelate-functionalized targeting agent present in the third vial is prostate-specific membrane antigen (PSMA)-targeting peptide, more preferably PSMA-11.

In particular embodiments, the metal inhibitor present in the third vial is selected from the group comprising: DOTA and its derivatives, DTPA and its derivatives, and sugars. In particular embodiments, the third vial of the kit further comprises a cryoprotectant. The cryoprotectant typically allows stabilizing the chelate-functionalized targeting agent and/or the metal inhibitor during lyophilisation. Non-limiting examples of suitable cryoprotectants are dimethyl sulphoxide (DMSO), glycerol (Gl), sucrose, sugars and mannitol.

In particular embodiments, the metal inhibitor is sugar selected from the group comprising: monosaccharides and their derivatives, disaccharides and their derivatives, and polysaccharides and their derivatives and sulfated sugars.

In particular embodiments, the metal inhibitor is selected from the group comprising: Glucose, Fructose, Beta-cyclodextrin, D-Mannose, and Sulfated sugars.

In particular embodiments, the radiolabelling kit as taught herein further comprises one or more, preferably all, of the list consisting of:
- a needleless transfer device for connecting two vials;
- an extension line comprising a proximal end adapted for connecting the extension line to the vial adapter and a distal end adapted for connecting the extension line to the needleless syringe;
- a vial adapter adapted for connecting the extension line or a needleless syringe to a vial; and/or
- a needleless syringe.

The term "needleless transfer device" as used herein refers to a device which avoids the necessity to utilize a needle in conjunction with a syringe for purposes of transferring and/or injecting a liquid medium from one environment (e.g., a first vial) into another environment, (e.g., a second vial) by interconnecting both environments and allowing a fluid communication from one to the other environment. A needleless transfer device may comprise at least one (such as one or two) holder(s) for a container into which or from which a liquid is to be transferred (e.g., a vial); a hollow enclosure for holding the valve mechanism and a hollow spike member for piercing the closure of a container, wherein said hollow spike member is in fluid communication with the hollow enclosure for holding the valve mechanism. If the needless transfer device comprises two holders for a vial, these two holders may hold vials with the same or different diameters. For example, both holders may fit a vial with a diameter of 20 mm or one holder may hold a vial with a diameter of 20 mm, while the other socket may hold a vial with a diameter of 13 mm.

In particular embodiments, the needleless transfer device comprises two vial connections, a valve and a luer-lock.

In particular embodiments, the valve can be configured to be in fluid communication with a first vial attached to the needleless transfer device and the luer-lock, in fluid communication with a second vial attached to the needleless transfer device and the luer-lock, or in fluid communication with the first and second vials attached to the needleless transfer device and the luer-lock.

In particular embodiments, the needleless transfer device is a needleless transfer device of Medimop Medical Projects LTD with reference number 7070105.

The term "extension line" as used herein refers to a tubing system which is at one end connectable to a first environment and at another end connectable to a second environment, and which brings the first and second environment in fluid communication. An extension line allows transferring and/or injecting a liquid medium from one environment (e.g., a first vial) into another environment, wherein said two environments separated by a distance, wherein said distance is at most the length of the extension line. The extension line may further comprise further ends connectable to a third environment, a fourth environment, a fifth environment etc. For example, the first environment may be a vial and the second environment may be a needleless syringe. If the first or second environment is a vial, the extension line may be connected to the vial directly or via a vial adaptor.

In particular embodiments, the extension line comprises a proximal end adapted for connecting the extension line to a vial adapter and a distal end adapted for connecting the extension line to a needleless syringe.

In particular embodiments, the extension line is a B-safe extension line-smallbore of Bicakcilar with reference number 13100101.

The term "vial adapter" as used herein refers to a device for connecting a vial to another vial, for connecting a vial to a needleless syringe or for connecting a vial to an extension line and to allow withdrawal of at least one dose of the vial content. A vial adaptor typically comprises a sharp, thin, hollow piercing spike that allows the adapter to penetrate the stopper/cover of the vial.

In particular embodiments, the vial adapter is a vial adapter of Medimop Medical Projects LTD with reference number 8072026.

In particular embodiments, the needleless syringe is a needleless syringe with a volume of at least 5 ml, at least 10 ml or at least 15 ml. For example, a needleless syringe with a volume of 10 ml, 12 ml or 15 ml.

In particular embodiments, the needleless syringe is a 10 ml (12 ml) Norm Ject needleless syringe of Henke Sass Wolf with reference number 4100.X00V0.

The radiolabelling kit as taught herein allows to easily radiolabel a chelate-functionalized targeting agent, shortens the synthesis time of the radiolabelled chelate-functionalized targeting agent and avoids the need of expensive hardware. A further aspect provides the use of the kit as taught herein for radiolabelling a chelate-functionalized targeting agent with gallium-68 carried out at a temperature near or equal to room temperature.

A further aspect provides a method for radiolabelling a chelate-functionalized targeting agent with gallium-68, comprising the elution of a gallium-68 generator with HCL, in a kit or an assembly as taught herein.

The invention further provides an assembly comprising a vial and a self-shielded device configured to hold a vial.

In particular embodiments, the assembly further comprises an extension line comprising a proximal end adapted for connecting the extension line to a vial (directly or via a vial adapter) within the self-shielding device and a distal end adapted for connecting the extension line to an environment external of the self-shielded device (e.g., to a needleless syringe or a gallium-68 generator). In more particular embodiments, the extension line comprises a proximal end adapted for connecting the extension line to a vial adapter and a distal end adapted for connecting the extension line to a needleless syringe.

In particular embodiments, the self-shielded device comprises a support (2) and a container unit (4), wherein said container unit comprises a lid (3) and a vessel comprising a void space dimensioned to hold a vial.

In particular embodiments, the support (2) comprises a base (1). The base typically provides a stable surface for placing the self-shielded device on a surface, such as a bench.

In particular embodiments, the dimensions of the base are equal to or at least 1%, at least 2%, at least 3%, at least 4%, at least 5%, at least 6%, at least 7%, at least 8%, at least 9%, or at least 10% larger than the dimensions of the top surface or bottom surface of the container unit. In particular embodiment, the container unit has a cylindrical shape and the base has a circular shape, wherein the diameter of the base is equal to or larger than the diameter of the container.

In particular embodiments, the base does not contact the container unit. In more particular embodiments, the space between the base and the container unit is such that the latter can be freely rotated with respect to the support means. In particular embodiment, said distance can be at least 1 cm, at least 2 cm, at least 3 cm, at least 4 cm, or at least 5 cm, in inverted and non-inverted configuration.

In particular embodiments, the support comprises extending from the base and in fixed relation to the base at least one longitudinal member (6), preferably one longitudinal member. In more particular embodiments, the at least one longitudinal member is positioned perpendicularly to the base and to a central axis of the vial and/or container.

In particular embodiments, the self-shielded device is an invertible self-shielded device.

In particular embodiments, the at least one longitudinal member is provided in revolute attachment with respect to the vessel, where an axis of rotation is horizontal, non-parallel to a central axis of the vial and/or parallel to an underside of the base.

In particular embodiments, the at least one longitudinal member is provided in revolute attachment with respect to the vessel by at least one, preferably one, pivoting means (e.g., a pivote point).

In particular embodiments, the at least one longitudinal member is dimensioned to allow a rotation of the container unit by more than 90 degrees, such as at least 120 degrees, at least 150 degrees, at least 160 degrees, at least 170 degrees or at least 180 degrees.

In particular embodiments, rotation of the container unit around the at least one pivoting means (e.g., pivot point) can be blocked by blocking means, such as by a tightenable pin (e.g., a screw or a clip).

In particular embodiments, the container unit is cylindrical shaped.

In particular embodiments, the container unit a height of at least 10 cm, at least 15 cm, at least 20, or at least 25 cm, preferably at least 15 cm. For example, the container unit may have a height of 15 cm, 16 cm, 17 cm, 18 cm, 19 cm or 20 cm.

In particular embodiments, the container unit has a diameter of at least 10 cm, at least 15 cm, or at least 20 cm, preferably at least 10 cm. For example, the container unit may have a diameter of 10 cm, 11 cm, 12 cm, 13 cm, 14 cm or 15 cm.

In particular embodiments, the void space has at least one side wall, preferably one side wall. In more particular embodiment, the at least one side wall has a thickness of at least 2 cm, at least 3 cm, at least 4 cm or at least 5 cm. For example, the at least one side wall may have a thickness of 2 cm, 3 cm, 4 cm, 5 cm, 6 cm or 7 cm.

In particular embodiments, the at least one side wall of the void space consists of a radiation shielding material, for example lead or tungsten.

In particular embodiments, the void space dimensioned to hold a vial is connected to the exterior with an opening. The opening can be shielded from the exterior of the container with the lid.

In particular embodiments, the dimensions of the void space suitable for holding the vial are at most 2%, at most 3%, at most 4%, at most 5%, at most 6%, at most 7%, at most 8%, at most 9%, or at most 10% larger than the dimensions of the vial. The void space specifically adapted to hold the vial allows to easily and firmly position the vial within the self-shielded device.

In particular embodiments, the void space suitable for holding the vial has a height of at least 4 cm, at least 5 cm, at least 6 cm, at least 7 cm, at least 8 cm, at least 9 cm or at least 10 cm. For example, the void space may have a height of about 5 cm, 5.5 cm, 6 cm, 6.5 cm, 7 cm, 7.5 cm, or 8 cm.

In particular embodiments, the void space suitable for holding the vial has a diameter of at least 1.5 cm, at least 2 cm, at least 2.5 cm, or at least 3 cm. For example, the void space may have a diameter of about 2 cm, 2.5 cm, 3 cm, 3.5 cm, or 4 cm.

In particular embodiments, the lid is provided with a further pivoting means (5) and/or is in revolute attachment with respect to the vessel, where an axis of rotation is vertical, parallel to a central axis of the vial and/or non-parallel to an underside of the base.

In particular embodiments, the lid is provided in revolute attachment with respect to the vessel by at least one, preferably one, pivot point.

In particular embodiment, the container unit, preferably the vessel, is provided with a channel configured to hold a dismountable conduit such as the extension line referred to above, for connecting the vial (directly or via a vial adapter) within the self-shielding device to an environment external of the self-shielded device (e.g., to a needleless syringe or a gallium-68 generator). Typically one end of the conduit is adapted for connecting the conduit to the vial in the void space and the other end of the conduit is located adapted for connecting the conduit to an environment external of the self-shielded device (e.g., to a needleless syringe or a gallium-68 generator). For example, the container unit may be provided with a channel configured to hold an extension line comprising a proximal end adapted for connecting the extension line to a vial (or a vial adapter) and a distal end adapted for connecting the extension line to an environment external of the self-shielded device (e.g. to a needleless syringe, a second conduit or a gallium-68 generator). The channel is configured to hold a dismountable conduit and prevents that the dismountable conduit hinders the sealing of the vessel by the lid, while still allowing a fluid communication between the vial and the environment externally of the container unit. Furthermore, the channel configured to hold a dismountable conduit allows the injection of fluids into and the elution of fluids from the vial located within the container unit in a more convenient manner, without being exposed to a source of radioactivity contained within the vial.

In particular embodiment, the channel configured to hold a dismountable conduit is provided at the interface of the lid (3) and the container vessel (4).

In particular embodiment, a side wall of the void space is provided with the channel configured to hold a dismountable conduit at the interface of the lid and the container vessel. The channel configured to hold a dismountable conduit may have one end at the interface of the void space and the sidewall of the vessel and one end at the interface of the sidewall of the vessel and the exterior of the vessel. In particular embodiments, the depth of the channel is equal to or larger than the diameter of the dismountable conduit. In particular embodiments, the depth of the channel is at least 2 mm, at least 3 mm, at least 4 mm, at least 5 mm, at least 6 mm, at least 7 mm, at least 8 mm, at least 9 mm or at least 10 mm.

In particular embodiments, the self-shielded device comprises a heating device. In particular embodiments, said heating device is capable of heating its contents to a temperature of from 40 to 120° C., preferably from 70 to 110° C., and more preferably from 85 to 100° C.

In particular embodiments, the self-shielded device comprises a system to measure the radioactivity contained within the vial located within the self-shielded container.

In particular embodiments, the self-shielded device is a self-shielded dispensing device.

A further aspect provides the use of the assembly as taught herein for radiolabelling a chelate functionalized targeting agent with gallium-68 carried out at a temperature near or equal to room temperature.

A further aspect provides a method for radiolabelling a chelate-functionalized targeting agent with gallium-68, comprising the elution of a gallium-68 generator with an eluent comprising HCl, in an assembly as taught herein.

The invention also discloses a self-shielded device as described herein with regard to the assembly.

The invention further provides a method for radiolabelling a targeting agent with gallium-68, said method comprising the elution of a gallium-68 generator with an eluent comprising an acid, in a kit as described herein, e.g. comprising the metal inhibitor, the chelate-functionalized targeting agent and acetate salt.

As indicated above, when the chelate-functionalized targeting agent is included in the kit, a gallium-68 generator can be eluted directly into the kit. In other embodiments, the chelate-functionalized targeting agent can be added to a kit comprising the acetate salt and a metal-inhibiting agent as described herein, prior to elution.

In some embodiments, the gallium-68 generator is eluted directly into the kit. In other embodiments, water is added to the solution prior to elution.

In some embodiments of the present invention, an appropriate amount of HCl is added to the solution prior to elution. Said HCl is added to partially neutralize the acetate. The amount of HCl added, preferably partially neutralizes the quantity of acetate salt in such a manner that the remaining quantity of acetate salt, i.e. unneutralized acetate salt, is able to balance the pH of said amount of HCl from the generator eluate (and thus dedicated to one type or brand of given generator) such that the pH of the solution obtained for the radiolabelling reaction or chelating reaction, resulting from the addition of HCl and the generator eluate in the kit as described herein, is in a pH range between 3 and 5, preferably between 3.5 and 4.5, preferably between 3.9 and 4.3. Said HCl may be added directly to the solution, or after a certain amount of water is added to said kit.

All gallium-68 generator may be used in the methods of the present invention. Typically, a commercial gallium-68 generator comprises a column on which the germanium-68 is fixed. A gallium-68 generator is typically eluted with an eluent comprising an acid, preferably HCl. Therefore, in preferred embodiments of the method, as taught herein, the gallium-68 generator is eluted with an eluent comprising HCl.

After elution of the gallium-68 generator in the kit as described herein, the solution obtained is left to react in the radiolabelling reaction for a short period of time, in particular between about 2 minutes and about 60 minutes, preferably from about 2 minutes to about 30 minutes, for example about 10 minutes.

Preferably, the radiolabelling reaction or chelation is performed at a temperature below 50° C., preferably of below 45° C., below 40° C., below 35° C., or below 30° C., most preferably at room temperature, e.g. between 20 and 25° C.

Preferably, the radiolabelling reaction or chelation is performed at a pH between about 3 and about 5, more preferably between about 3.5 and about 4.5, more preferably between about 3.9 and about 4.3.

The invention further provides a method for radiolabelling a chelate-functionalized targeting agent with a radionuclide, preferably gallium-68, comprising the following sequential steps:
  reconstituting lyophilized a chelate-functionalized targeting agent and a lyophilized metal inhibitor with a buffering medium, preferably an acetate buffer;
  adding the buffering medium, and the reconstituted chelate-functionalized targeting agent and metal inhibitor to an eluate of a radioactive metal generator, preferably a gallium-68 generator; and
  allowing radiolabelling of the chelate-functionalized targeting agent with the radioactive metal, preferably gallium-68 for about 1 minute or up to about 5 or 10 minutes.

In particular embodiments, the buffering medium allows to maintain the pH in the range 3-8, more preferably in the range of 3-5.

In particular embodiments, the buffering medium consists of phosphate, nitrate, HEPES, acetate, TRIS, ascorbate, or, citrate or a mixture thereof.

In particular embodiments, the radioactive metal is selected from the group comprising: copper-64, gallium-68, gallium-67, gallium-66, lutecium-177, yttrium-86, yttrium-90, indium-114, indium-111, scandium-47, scandium-44, scandium-43, zirconium-89, bismuth-213, bismuth-212, actinium-225, lead-212, rhenium-188, rhenium-186, and rubidium-82.

In particular embodiments, the method for radiolabelling a chelate-functionalized targeting agent with a radioactive metal, preferably gallium-68, comprises:
  recovering an eluate of a radioactive metal generator, preferably a gallium-68 generator, into a first vial located within a self-shielded device, preferably wherein said first vial is a vacuumed vial;
  adding a suitable amount of a buffering medium to the lyophilized chelate-functionalized targeting agent and lyophilized metal inhibitor comprised in a second vial to balance the pH of the eluate from a gallium-68 generator to a pH value ranging from 3 to 5 when said mixture of buffering medium, chelate-functionalized targeting agent and metal inhibitor is contacted with the eluate, preferably wherein said buffering medium is an acetate buffer;
  recovering the mixture of buffering medium, chelate-functionalized targeting agent and metal inhibitor from the second vial;
  adding the mixture of buffering medium, chelate-functionalized targeting agent and metal inhibitor to the recovered eluate of the radioactive metal generator, preferably gallium-68 generator, comprised in the first vial located within the shielding device; and
  allowing radiolabelling of the chelate-functionalized targeting agent with the radioactive metal, preferably gallium-68, for about 1 minute or up to about 5 or 10 minutes.

In particular embodiments, the first vial (containing a vacuum) is connected to a vial adapter which is connected to an extension line comprising a proximal end adapted for connecting the extension line to the vial adapter and a distal end adapted for connecting the extension line to a needleless syringe; wherein said distal end is located outside the self-shielded device.

In particular embodiments, the suitable amount of buffering medium, preferably acetate buffer, is contained in a third container and the suitable amount of buffering medium is added to the lyophilized chelate-functionalized targeting agent and lyophilized metal inhibitor by interconnecting said second and third vials via a needleless transfer device. In more particular embodiments, the needleless transfer device comprises a valve and a luer-lock, preferably wherein said valve can be configured to be in fluid communication with the third vial and the luer-lock, the second vial and the luer-lock, or the third and second vials and the luer-lock.

In particular embodiments, the step of adding a suitable amount of buffering medium, preferably acetate buffer present in a third vial, to the lyophilized chelate-functionalized targeting agent and lyophilized metal inhibitor comprised in a second vial comprises:
  interconnecting said third vial comprising the buffering medium, preferably acetate buffer, and the second vial comprising lyophilized chelate-functionalized targeting agent and lyophilized metal inhibitor by a needleless transfer device; wherein the third vial is located above the second vial, wherein the luer-lock is capped, and wherein said valve can be configured to be in fluid communication with the third vial and the luer-lock, the second vial and the luer-lock, or the third and second vials and the luer-lock;
  allowing the buffering medium, preferably acetate buffer, to flow from the third vial to the second vial through the valve of the needleless transfer device which is configured to be in fluid communication with the third and second vials and the luer-lock; and mixing the buffering medium, preferably acetate buffer, lyophilized chelate-functionalized targeting agent and lyophilized metal inhibitor.

In particular embodiments, the step of recovering the mixture of buffering medium, preferably acetate buffer, chelate-functionalized targeting agent and metal inhibitor from the second vial comprises:
configuring the valve of the needleless transfer device to be in fluid communication with the second vial and the luer-lock, but not in fluid communication with the third vial, wherein the luer-lock is capped;
uncapping the luer-lock;
connecting a needleless syringe comprising air in a volume which is at least 50% the volume of the second vial to the uncapped luer-lock;
injecting the air in a volume which is at least 50% the volume of the second vial from the needleless syringe into the second vial via the uncapped luer-lock;
turning the third vial and the second vial interconnected by the needleless transfer device so that the second vial is located above the third vial; and
withdrawing the mixture of buffering medium, preferably acetate buffer, chelate-functionalized targeting agent and metal inhibitor from the second vial via the uncapped luer-lock, using the needleless syringe.

In particular embodiments, the step of adding the mixture of buffering medium, preferably acetate buffer, chelate-functionalized targeting agent and metal inhibitor to the recovered eluate of the radioactive metal generator, preferably gallium-68 generator, comprised in the first vial located within the self-shielded device comprises injecting the mixture of acetate buffer, chelate-functionalized targeting agent and metal inhibitor into the first vial located within the self-shielded device using a needleless syringe.

In particular embodiments, the step of allowing radiolabelling of the chelate-functionalized targeting agent with the radioactive metal, preferably gallium-68, is performed for at least 30 seconds, at least 40 seconds, at least 50 seconds, at least 1 minute, at least 2 minutes, at least 3 minutes, at least 4 minutes, at least 5 minutes, at least 6 minutes, at least 7 minutes, at least 8 minutes, at least 9 minutes or at least 10 minutes, preferably for at least 5 minutes.

In particular embodiments, all steps of the method for radiolabelling a targeting agent with gallium-68 are carried out at a temperature of below 50° C., preferably of ambient or room temperature (e.g. of between 20 and 30° C.).

In particular embodiments, the self-shielded device comprises a container unit comprising a void space dimensioned to hold a vial, wherein said container unit is rotatable and/or invertible around a horizontal axis. In further particular embodiments, the method for radiolabelling a targeting agent with a radioactive metal, preferably gallium-68, further comprises after the step of allowing radiolabelling of the chelate-functionalized targeting agent with the radioactive metal, preferably gallium-68, inverting the container unit, thereby also inverting the first vial located within the self-shielded device.

In particular embodiments, the method for radiolabelling a chelate-functionalized targeting agent with a radioactive metal, preferably gallium-68, further comprises withdrawing the radioactive metal-labelled, preferably gallium-68-labelled, chelate-functionalized targeting agent from the first vial, preferably via the distal end of the extension line. The inversion of the first vial comprising the radioactive metal-labelled, preferably gallium-68-labelled, chelate-functionalized targeting agent allows to withdraw a dose of the radioactive metal-labelled chelate-functionalized targeting agent or to guide a dose of the radioactive metal-labelled chelate-functionalized targeting agent to a patient by using the force of gravity, thereby avoiding the need to pressurize the first vial comprising the radioactive metal-labelled chelate-functionalized targeting agent (for example by use of a pump) and reducing risk of exposure of the user to radioactive material.

The invention also encompasses the solution obtained by elution of a gallium-68 generator with an eluent comprising an acid, preferably HCl, in a kit as taught herein.

Preferably, said solution has a pH between about 3 and about 5, preferably between about 3.5 and about 4.5, more preferably between about 3.9 and about 4.3.

The invention also discloses a gallium-68 radiolabeled targeting agent, obtained by anyone of the methods as described herein.

In one aspect, the invention also provides a preparation method of a kit as described herein, said method comprising the steps of:
a) preparing a solution comprising the acetate salt, a chelate-functionalized targeting agent and an inhibitor of metal; and
b) lyophilizing the solution obtained in step a).

Alternatively, the invention further provides a process for preparing a kit of the invention comprising the steps of:
a) preparing a solution comprising a chelate-functionalized targeting agent and an inhibitor of metal; and
b) lyophilizing the solution obtained in step a).
c) adding the acetate salt as a powder in the obtained lyophilized product in step b).

Further alternatively, the invention further provides a process for preparing a kit of the invention comprising the steps of:
a) preparing a solution comprising a chelate-functionalized targeting agent and an inhibitor of metal; and
b) lyophilizing the solution obtained in step a).
c) adding an acetate buffer in the obtained lyophilized product in step b).

Finally, the invention further provides a process for preparing a kit of the invention comprising the steps of:
a) preparing a solution comprising the acetate salt, a chelate-functionalized targeting agent and an inhibitor of metal; and
b) optionally freeze the solution obtained in step a).

While the invention has been described in conjunction with specific embodiments thereof, it is evident that many alternatives, modifications, and variations will be apparent to those skilled in the art in light of the foregoing description. Accordingly, it is intended to embrace all such alternatives, modifications, and variations as follows in the spirit and broad scope of the appended claims.

The above aspects and embodiments are further supported by the following non-limiting examples.

EXAMPLES

Example 1: Generator E & Z/NODAGA Peptide without Metal Inhibitor

Labelling a Peptide with a 68Ga Eluate of 5 mL of 0.1 M HCl

A commercial gallium-68 generator 1850 MBq (Eckert & Ziegler) is eluted with 5 mL of 0.1M HCl (Ultrapure grade) directly into a flask containing 150 mg of sodium acetate (Ultrapure grade) lyophilized, 240 µl of HCl 3M (Ultrapure grade), 760 µl of Milli-Q and 50 µg lyophilized NODAGA-NOC. The flask was left for 10 min at room temperature. The product is obtained with a radiochemical purity of 64% according to TLC analysis of the reaction medium.

Example 2: Similarly to What was Done in Example 1 Different Combinations were Tested and are Summarized in the Table Below

| Entry | Acetate | Chelating agent use in the chelate-functionalized targeting agent | Inhibitor | Generator | Radiolabelling yield for 10 minutes, room T° vs radiolabelling yield without metal inhibitor using similar conditions | Generator cleaniliness | Kit Preparation* |
|---|---|---|---|---|---|---|---|
| 1 | 150 mg | NOTA 25 µg | DOTA | E&Z | 82% vs 51% | Generator cleaned | A |
| 2 | 150 mg | NOTA 25 µg | Fructose | E&Z | 87% vs 51% | Generator cleaned | A |
| 3 | 150 mg | NOTA 25 µg | Beta-cyclo-dextrin | E&Z | 83% vs 51% | Generator cleaned | A |
| 4 | 150 mg | NODAGA 25 µg | Beta-cyclo-dextrin | E&Z | 95% vs 64% | Generator cleaned | A |
| 5 | 150 mg | HBED 25 µg | Beta-cyclo-dextrin | E&Z | 91% vs 77% | Generator cleaned | A |
| 6 | 150 mg | HBED 25 µg | Fructose | E&Z | 94% vs 77% | Generator cleaned | A |
| 7 | 150 mg | NOTA 10 µg | Fructose | E&Z | 85% vs 39% | Generator cleaned | A |
| 9 | 150 mg | NODAGA 10 µg | Beta-cyclo-dextrin | E&Z | 84% vs 55% | Generator cleaned | A |
| 9 | 150 mg | HBED 10 µg | Beta-cyclo-dextrin | E&Z | 87% vs 51% | Generator cleaned | A |
| 10 | 150 mg | NODAGA 50 µg | Beta-cyclo-dextrin | ITG | 94% vs 46% | Generator cleaned | A |
| 11 | 150 mg | NODAGA 50 µg | Beta-cyclo-dextrin | E&Z | 97% vs 70% | Generator cleaned | A |
| 12 | 150 mg | NODAGA 50 µg | D-Mannose | E&Z | 91% vs 44% | Generator not cleaned | A |
| 13 | 150 mg | NODAGA 50 µg | DOTA | E&Z | 95% vs 70% | Generator cleaned | A |
| 14 | 150 mg | NODAGA 50 µg | Beta-cyclo-dextrin | iThemba | 91% vs 61% | Generator cleaned | A |
| 15 | 150 mg | NODAGA 50 µg | Fructose | E&Z | 95% vs 70% | Generator cleaned | A |
| 16 | 150 mg | HBED 20 µg | DOTA | ITG | 91% vs 75% | Generator cleaned | A |
| 17 | 150 mg | NODAGA 25 µg | D-Mannose | ITG | 95% vs 60% | Generator cleaned | A |
| 18 | 150 mg | NODAGA 25 µg | Beta-cyclo-dextrin | ITG | 96% vs 60% | Generator cleaned | A |
| 19 | 150 mg | NODAGA 25 µg | tetra-tBu-DTPA | ITG | 89% vs 60% | Generator cleaned | A |
| 20 | 150 mg | NODAGA 25 µg | Beta-cyclo-dextrin | ITG | 96% vs 61% | Generator cleaned | B |
| 21 | 150 mg | NODAGA 25 µg | DOTA | E&Z | 94% vs 64% | Generator cleaned | B |
| 22 | 150 mg | NODAGA 25 µg | DOTA | E&Z | 89% vs 64% | Generator cleaned | C |

-continued

| Entry | Acetate | Chelating agent use in the chelate-functionalized targeting agent | Inhibitor | Generator | Radiolabelling yield for 10 minutes, room T° vs radiolabelling yield without metal inhibitor using similar conditions | Generator cleaniliness | Kit Preparation* |
|---|---|---|---|---|---|---|---|
| 23 | 150 mg | NODAGA 25 µg | Glucose | ITG | 89% vs 61% | Generator cleaned | C |
| 24 | 150 mg | DFO 10 µg | DOTA | ITG | 98% vs 85% | Generator cleaned | A |

*A = a preparation method comprising the steps of: a) preparing a solution comprising the acetate salt, a chelate-functionalized targeting agent and an inhibitor of metal; and b) lyophilizing the solution obtained in step a).
B = a preparation method comprising the steps of: a) preparing a solution comprising a chelate-functionalized targeting agent and an inhibitor of metal; and b) lyophilizing the solution obtained in step a). c) adding the acetate salt as a solid
C = a preparation method comprising the steps of: a) preparing a solution comprising a chelate-functionalized targeting agent and an inhibitor of metal; and b) lyophilizing the solution obtained in step a). c) adding the acetate salt as a buffer solution adapted to the generator used To conclude, the results above clearly show the increased gallium-68 radiolabelling yield of about 90% or more in all set-ups where a metal inhibitor as defined herein is used in addition to the chelator-functionalized targeting agent. If said agent is not added, much lower yields are obtained. The yield is virtually independent of the use of acetate in solid form or in buffer form. Also when the acetate salt is co-lyophilized with the metal inhibitor and the chelator-functionalized targeting agent, a very good yield is obtained.

Example 3: Radiolabeling PSMA-11 with Gallium-68

1. Transfer of Gallium-68 into a Sterile Vacuumed Vial (Vial 1)

Step 1. Removing the cover from the vial adapter package, while not removing the vial adapter from the blister package.
Step 2. Attaching the vial adapter to the sterile vacuumed vial (vial 1), using the blister pack as a holder. Seating the vial adapter on the sterile vacuumed vial by pushing down until the spike penetrates the rubber stopper and the vial adapter snaps in place.
Step 3. Removing the blister package.
Step 4. Taking the extension line from its package and attaching it to the swabable vial adapter.
Step 5. Placing the sterile vacuumed vial in the self-shielded dispensing device as described herein.
Step 6. Transferring up to 1.85 GBq of gallium chloride dissolved in 1.1 ml of 0.1 M hydrochloric acid Ph. Eur. Inside the sterile vacuumed vial through the extension line.

2. Transfer of PSMA-11 and Acetate Buffer into the Sterile Vacuumed Vial

Figure 2A:
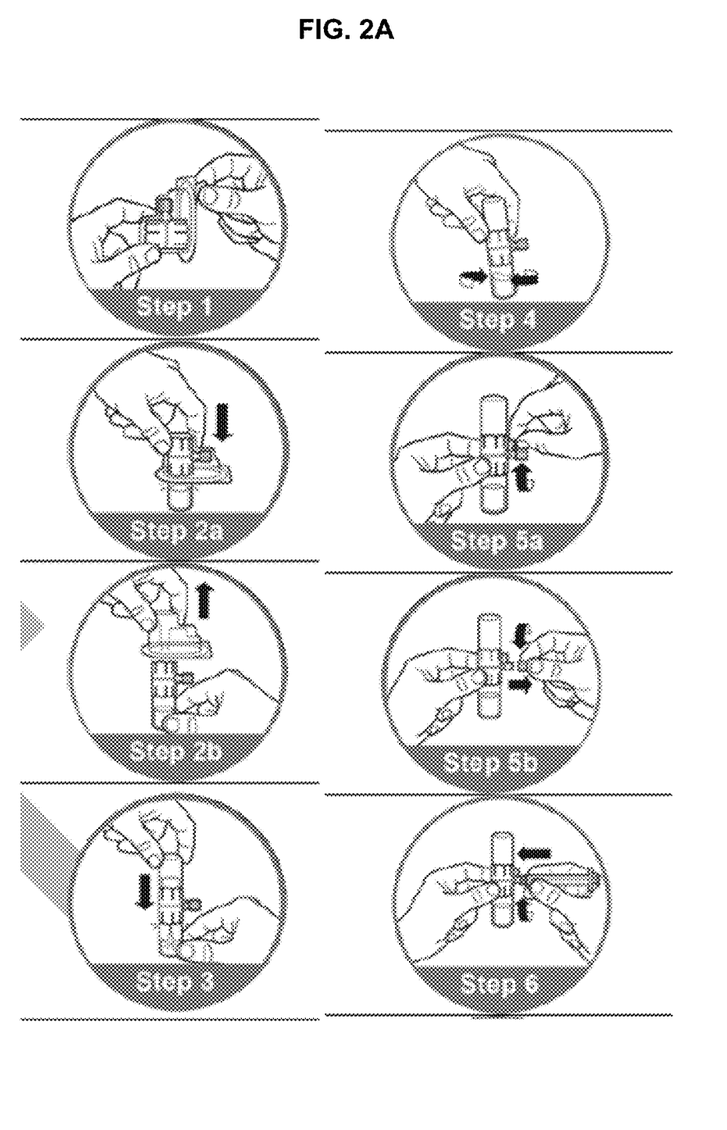
FIG. 2A-2B shows an exemplary schematic representation of the steps of a method for radiolabeling PSMA-11 with gallium-68 using a needleless transfer device as taught herein. (A) Steps 1-6; (B) Steps 7-9.
Figure 2B:
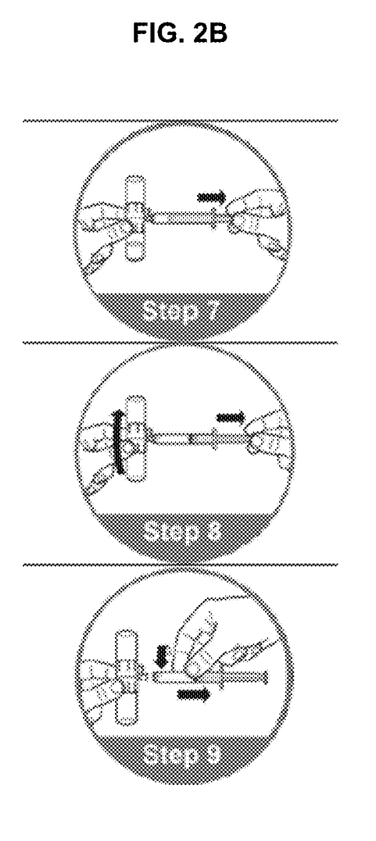

Step 1. Removing the cover from the needleless transfer device package, while not removing the needleless transfer device from the blister package (FIG. 2, Step 1).
Step 2a: Placing the device on top of the sterile acetate buffer vial (vial 2), Configuration B, using the blister pack as a holder. Seating the device on the sterile acetate buffer vial, Configuration B by pushing down until the spike penetrates the rubber stopper and the device snaps in place (FIG. 2, Step 2a).
Step 2b. Removing the needleless transfer device from the blister pack (FIG. 2, Step 2b).
Step 3. Inverting the sterile acetate buffer vial, Configuration B with the needleless transfer device attached; seating the open end of the device on the PSMA-11 sterile vial (vial 3) by pushing down until the spike penetrates the rubber stopper and the device snaps in place. Acetate buffer will flow into the PSMA-11 sterile vial (FIG. 2, Step 3).
Step 4. Gently swirling the vials to make sure the product is thoroughly mixed (FIG. 2, Step 4).
Step 5a. Turning the valve on the side of the device in medium position (FIG. 2, Step 5a).
Step 5b. Removing the cap from the luer connector (FIG. 2, Step 5b).
Step 6. Removing the 10 mL syringe's protective cap. Connecting the 10 mL syringe to the luer lock by turning it clockwise (FIG. 2, Step 6).
Step 7. Pulling back on the plunger (FIG. 2, Step 7).
Step 8. Turning the system so the PSMA-11 sterile vial is on top. Pulling back on the plunger to withdraw the solution (FIG. 2, Step 8).
Step 9. Removing the syringe from the device (FIG. 2, Step 9).

3. Radiolabelling and Quality Control

Step 1. Attaching the 10 mL syringe containing PSMA-11 dissolved in acetate buffer to the extension line and transferring its content inside the sterile vacuumed vial (vial 1).
Step 2. Incubating for 5 minutes.
Step 3. Collecting 50 µL of the sterile vacuumed vial content using the 10 ml syringe and removing the syringe from the extension line.
Step 4. Performing a quality control.

Figure 3:
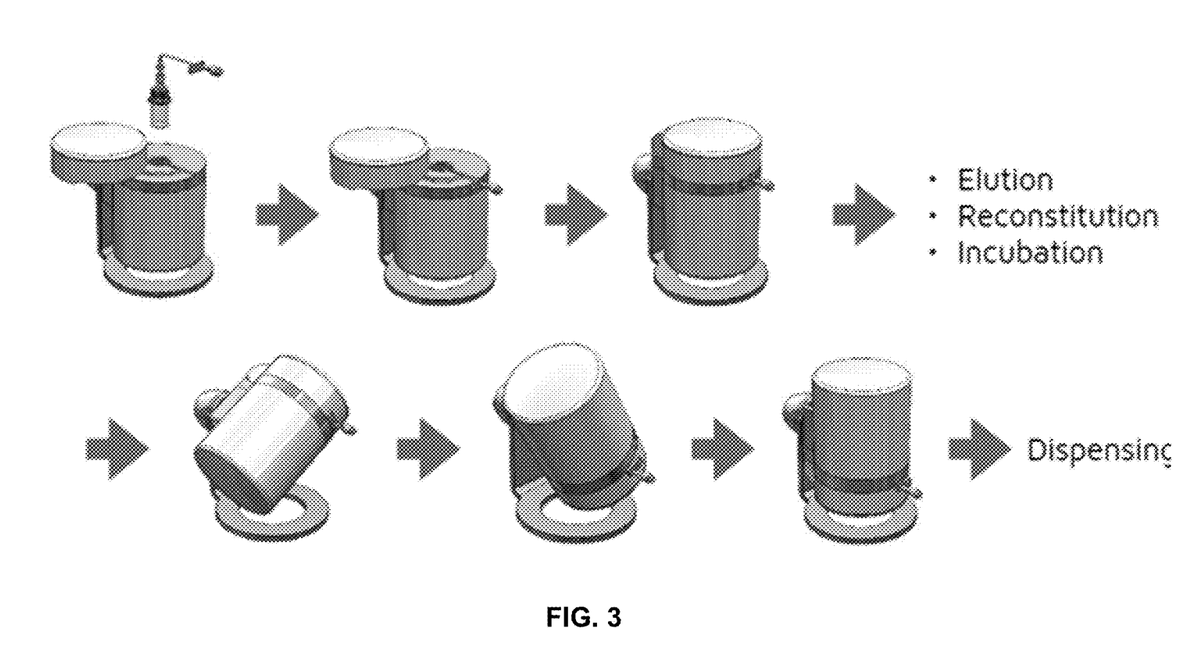
FIG. 3 shows an exemplary schematic representation of a method for radiolabeling PSMA-11 with gallium-68 using a needleless transfer device and an invertible self-shielded device as taught herein.

Example 4: Radiolabelling PSMA-11 with Gallium-68 Using the Self-Shielded Dispensing Device as Taught Herein First, the lid of the container unit is opened and a sterile vacuumed vial (vial 1) attached to an extension line by a vial adapter is placed into the void space dimensioned to hold a vial of the self-shielded dispensing device as taught herein (FIG. 3).
Next, the lid of the container unit is closed and gallium-68 is transferred to the sterile vacuumed vial (vial 1) by connecting the extension line to a gallium-68 generator and eluting the gallium-68 eluate into the sterile vacuumed vial (FIG. 3).
Then, PSMA-11 and acetate buffer are mixed as described in steps 1 to 10 of Example x and the PSMA-11/acetate buffer mixture is transferred to the sterile vacuumed vial located within the self-shielded dispensing device by attaching the 10 mL syringe containing to the extension line and injecting the PSMA-11/acetate buffer mixture into the sterile vacuumed vial. The labelling of PSMA-11 with gallium-68 is allowed for 5 minutes at room temperature (FIG. 3).

Subsequently, the container unit is inverted and fixed at its inverted position. A single dose or multiple doses of gallium-68 labelled PSMA-11 can be dispensed from the self-shielded dispensing device by the extension line (FIG. 3).

The invention claimed is:

1. A method for radiolabelling a chelate-functionalized targeting agent with gallium-68, comprising
recovering an eluate of a gallium-68 generator into a first vial located within a self-shielded device;
adding a suitable amount of acetate buffer to a second vial comprising a lyophilized chelate-functionalized targeting agent and a lyophilized metal inhibitor to form a mixture comprising acetate buffer, chelate-functionalized targeting agent and metal inhibitor, wherein the acetate buffer is added in a suitable amount to balance the pH of the eluate from the gallium-68 generator to a pH value ranging from 3 to 5 when the mixture is contacted with the eluate;
recovering the mixture of acetate buffer, chelate-functionalized targeting agent and metal inhibitor from the second vial;
adding the mixture of acetate buffer, chelate-functionalized targeting agent and metal inhibitor to the recovered eluate of the gallium-68 generator in the first vial located within the shielding device; and
allowing radiolabelling of the chelate-functionalized targeting agent with gallium-68,
wherein said metal inhibitor is selected from the group consisting of: DOTA, glucose, fructose, beta-cyclodextrin, D-mannose, and tetra-tBu-DTPA, and
wherein said chelator in said chelate-functionalized targeting agent is selected from the group consisting of: NOTA, NODAGA, HBED and DFO.

2. The method according to claim 1, wherein the step of allowing radiolabelling of the chelate-functionalized targeting agent with gallium-68 is performed for at least 1 minute.

3. The method according to claim 1, wherein the first vial located within the self-shielded device is connected to a vial adapter which is connected to an extension line comprising a proximal end adapted for connecting the extension line to the vial adapter and a distal end adapted for connecting the extension line to a needleless syringe; wherein said distal end is located outside the self-shielded device.

4. The method according to claim 1, wherein the suitable amount of acetate buffer is contained in a third vial and the suitable amount of acetate buffer is added to the lyophilized chelate-functionalized targeting agent and lyophilized metal inhibitor by interconnecting said second and third vials via a needleless transfer device.

5. The method according to claim 4, wherein the needleless transfer device comprises a valve and a luer-lock.

6. The method according to claim 5, wherein the suitable amount of acetate buffer present in the third vial is added to the lyophilized chelate-functionalized targeting agent and lyophilized metal inhibitor in the second vial by:
interconnecting said third vial comprising the acetate buffer and the second vial comprising lyophilized chelate-functionalized targeting agent and lyophilized metal inhibitor by a needleless transfer device; wherein the third vial is located above the second vial, wherein the luer-lock is capped, and wherein the valve can be configured to be in fluid communication with the third vial and the luer-lock, the second vial and the luer-lock, or the third and second vials and the luer-lock;
allowing the acetate buffer to flow from the third vial to the second vial through the valve of the needleless transfer device which is configured to be in fluid communication with the third and second vials and the luer-lock; and
mixing the acetate buffer, lyophilized chelate-functionalized targeting agent and lyophilized metal inhibitor.

7. The method according to claim 5, wherein the step of recovering the mixture of acetate buffer, chelate-functionalized targeting agent and metal inhibitor from the second vial comprises:
configuring the valve of the needleless transfer device to be in fluid communication with the second vial and the luer-lock, but not in fluid communication with the third vial, wherein the luer-lock is capped;
uncapping the luer-lock;
connecting a needleless syringe comprising air in a volume which is at least 50% the volume of the second vial to the uncapped luer-lock;
injecting the air in a volume which is at least 50% the volume of the second vial from the needleless syringe into the second vial via the uncapped luer-lock;
turning the third vial and the second vial interconnected by the needleless transfer device so that the second vial is located above the third vial; and
withdrawing the mixture of acetate buffer, chelate-functionalized targeting agent and metal inhibitor from the second vial via the uncapped luer-lock, using the needleless syringe.

8. The method according to claim 1, wherein the step of adding the mixture of acetate buffer, chelate-functionalized targeting agent and metal inhibitor to the recovered eluate of the gallium-68 generator comprised in the first vial located within the self-shielded device comprises injecting the mixture of acetate buffer, chelate-functionalized targeting agent and metal inhibitor into the first vial located within the self-shielded device using a needleless syringe.

9. The method according to claim 1, wherein the self-shielded device comprises a container unit comprising a void space dimensioned to hold the first vial, wherein said container unit is rotatable around a horizontal axis.

10. The method according to claim 9, further comprising inverting the container unit; and
withdrawing the gallium-68-labelled chelate-functionalized targeting agent from the first vial.

11. The method according to claim 1, wherein the targeting agent of said chelate-functionalized targeting agent is prostate-specific membrane antigen (PSMA)-11.

12. An in vivo method for imaging a subject comprising the steps of:
1) producing gallium-68 radiolabelled PSMA-11 using the method of claim 11;
2) administering said gallium-68 radiolabelled PSMA-11 to the subject; and
3) detecting said gallium-68 radiolabelled PSMA-11 in the subject using positron emission tomography (PET).

* * * * *